(12) United States Patent
Cook et al.

(10) Patent No.: US 10,376,739 B2
(45) Date of Patent: Aug. 13, 2019

(54) BALANCE TESTING AND TRAINING SYSTEM AND METHOD

(71) Applicant: BALANCE4GOOD LTD., London (GB)

(72) Inventors: James Bingham Cook, London (GB); Jean Pierre Claude Farcy, Antibes (FR)

(73) Assignee: Balance4Good, Ltd., London (GB)

( * ) Notice: Subject to any disclaimer, the term of this patent is extended or adjusted under 35 U.S.C. 154(b) by 211 days.

(21) Appl. No.: 15/402,078

(22) Filed: Jan. 9, 2017

(65) Prior Publication Data

US 2017/0197115 A1    Jul. 13, 2017

Related U.S. Application Data

(60) Provisional application No. 62/276,418, filed on Jan. 8, 2016.

(51) Int. Cl.
 *A63B 24/00*  (2006.01)
 *A63B 26/00*  (2006.01)
 (Continued)

(52) U.S. Cl.
 CPC ........ *A63B 26/003* (2013.01); *A63B 24/0003* (2013.01); *A63B 24/0062* (2013.01);
 (Continued)

(58) Field of Classification Search
 CPC .......... A63B 2220/836; A63B 24/0062; A63B 26/003
 See application file for complete search history.

(56) References Cited

U.S. PATENT DOCUMENTS

| | | | |
|---|---|---|---|
| 8,123,527 B2 * | 2/2012 | Holljes | A63F 13/53 434/29 |
| 8,206,325 B1 | 6/2012 | Najafi et al. | |

(Continued)

OTHER PUBLICATIONS

International Search Report and Written Opinion dated May 30, 2017, for PCT/IB2017/000040.
(Continued)

*Primary Examiner* — Xuan M Thai
*Assistant Examiner* — Malina D. Blaise
(74) *Attorney, Agent, or Firm* — Pillsbury Winthrop; Shaw Pittman LLP

(57) ABSTRACT

A human balance testing and training system may comprise: a mobile communication device comprising: (1) sensors; (2) a display unit; (3) an input unit; (4) an evaluation subsystem for evaluating balance capabilities of a human subject utilizing data collected when the human subject is performing one or more balance evaluation exercises, the data including data received from the sensors; (5) an expert subsystem for prescribing an exercise plan; and (6) a training subsystem for maintaining an exercise plan including one or more balance training exercises for the human subject; wherein the exercise plan is determined by at least one of a balance evaluation by the evaluation subsystem, performance data provided by the training subsystem, and input from a health professional; and wherein the sensors are configured to measure movement of the human subject during performance of one or more of an evaluation exercise and a training exercise.

67 Claims, 2 Drawing Sheets

(51) Int. Cl.
  *A63B 71/06* (2006.01)
  *G06F 19/00* (2018.01)
  *G09B 19/00* (2006.01)
(52) U.S. Cl.
  CPC ...... *A63B 24/0075* (2013.01); *A63B 71/0622* (2013.01); *G06F 19/3481* (2013.01); *G09B 19/003* (2013.01); *A63B 2071/0625* (2013.01); *A63B 2220/22* (2013.01); *A63B 2220/30* (2013.01); *A63B 2220/836* (2013.01); *A63B 2225/20* (2013.01)

(56) References Cited

U.S. PATENT DOCUMENTS

| | | | |
|---|---|---|---|
| 8,845,556 B1 | 9/2014 | Schickler et al. | |
| 9,149,222 B1* | 10/2015 | Zets | A61B 5/16 |
| 9,974,478 B1* | 5/2018 | Brokaw | A61B 5/486 |
| 2003/0077556 A1* | 4/2003 | French | A61B 5/1113 434/258 |
| 2009/0098519 A1* | 4/2009 | Byerly | G09B 23/28 434/247 |
| 2010/0049096 A1* | 2/2010 | Ten Kate | G08B 21/0446 600/595 |
| 2011/0213278 A1* | 9/2011 | Horak | A61B 5/112 600/595 |
| 2012/0259648 A1* | 10/2012 | Mallon | G06F 19/3418 705/2 |
| 2013/0171596 A1* | 7/2013 | French | G09B 19/00 434/236 |
| 2014/0066816 A1* | 3/2014 | McNames | A61B 5/002 600/595 |
| 2014/0074180 A1* | 3/2014 | Heldman | A61B 5/1101 607/45 |
| 2014/0228712 A1* | 8/2014 | Elliott | A63B 71/06 600/587 |
| 2015/0040665 A1* | 2/2015 | Borkholder | A61B 5/002 73/510 |
| 2016/0058367 A1* | 3/2016 | Raghuram | A61B 5/486 600/479 |
| 2016/0166180 A1* | 6/2016 | Martin | A61B 5/112 702/141 |

OTHER PUBLICATIONS

Patel, Shyami, et al., "A Review of Wearable Sensors and Systems with Applications in Rehabilitation," JNER 2012, vol. 9, No. 21, published Apr. 20, 2012; 17 pages.

Ma, Christina Zong-Hao, et al., "Balance Improvement Effects of Biofeedback Systems with State of the Art Wearable Sensors; A Systematic Review;" Sensors, published Mar. 25, 2016, 34 pages.

* cited by examiner

BALANCE TESTING AND TRAINING SYSTEM AND METHOD

CROSS-REFERENCE TO RELATED APPLICATIONS

This application claims the benefit of U.S. Provisional Application No. 62/276,418 filed Jan. 8, 2016, incorporated by reference in its entirety herein.

FIELD OF THE INVENTION

The present invention relates generally to human balance testing and training systems and methods.

BACKGROUND

Loss of balance and the resulting injuries caused by falling is one of the most significant healthcare problems facing people as they age. About one in three people in England over the age of 65 fall at least once every year, and the results are often costly and life shortening. In the US the National Institute of Health (NIH) reports a similar fall rate for those over 65, and notes that a third of those falls result in moderate to severe injuries that can lead to further declines in health and loss of independence. The total cost of falls in the US and UK is roughly $60 billion per year.

Independence of people as they age is also an important problem. As people feel their sense of balance decline, they feel less confident in their ability to move about safely so they tend to not go outside and not walk around as much. This inactivity often leads to a sense of isolation, and also in fact can cause a further deterioration in the mobility of the individual.

Even at a younger age, improving balance can be very valuable for people. Although younger people may not have experienced a decrease in balance capabilities, better balance can lead to improved performance in sports, as well as providing the confidence to lead a fuller, more active life.

Currently, balance testing, evaluation and treatment are only available in specialty clinics and in certain doctor's offices. The testing, evaluation and treatment typically entail the person coming in to a clinic to meet with a doctor, followed by a series of tests on specially built equipment. The doctor evaluates the test results, and prescribes a series of exercises or activities to help the person improve their balance capabilities. For example, there are "balance classes" that are given at certain senior homes or community centers which are typically led by an instructor, and involve a variety of physical activities to build strength and improve balance.

The current evaluation process requires the use of expensive test machinery, and also the time of experts to manage the process. The training regime is similarly set up and monitored by experts. These experts are a scarce resource and therefore expensive. Furthermore, it is often required that the person physically go to a clinic or laboratory for this testing, evaluation and treatment.

As such, this sort of evaluation and treatment has been limited to a very small number of people, even though loss of balance is a population wide challenge. Most people with declining balance capabilities—and it is essentially everyone—never have the opportunity to test their balance, and never have access to a training program that is designed to help them improve their balance. By not having these opportunities, they are not able to prevent the decline of balance, and are therefore subject to the falls and decrease in confidence that poor balance brings.

Similarly, there is no self-managed balance improvement system available for younger people either. Anyone in this group wanting to improve balance usually has to retain the services of a specialist coach.

There is a need for a consumer product that: (1) allows persons on their own to effectively test their balance and (2) after evaluation of the test data, provides interactive exercises for the person to improve their balance.

SUMMARY OF THE INVENTION

According to some embodiments, a human balance testing and training system may comprise: a mobile communication device comprising: (1) sensors; (2) a display unit; (3) an input unit; (4) an evaluation subsystem for evaluating balance capabilities of a human subject utilizing data collected when the human subject is performing one or more balance evaluation exercises, the data including data received from the sensors; (5) an expert subsystem for prescribing an exercise plan; and (6) a training subsystem for maintaining an exercise plan including one or more balance training exercises for the human subject; wherein the exercise plan is determined by at least one of a balance evaluation by the evaluation subsystem, performance data provided by the training subsystem, and input from a health professional; and wherein the sensors are configured to measure movement of the human subject during performance of one or more of an evaluation exercise and a training exercise. The system may further comprise a remote subsystem on a remote server coupled to the mobile device by a wide area network, the remote subsystem being configured to receive data from the mobile device and send software updates to the mobile device for at least one of the evaluation subsystem, the expert subsystem and the training subsystem. The system may further comprise a remote interface coupled to the mobile device by a wide area network, the remote interface being configured to permit one or more of monitoring the performance of the human subject and controlling the evaluation and training of the human subject. The mobile device may further comprise an incentive subsystem for providing motivational messages to the human subject on the display unit of the mobile device.

According to some embodiments, a human balance testing and training system may comprise: sensors configured to be attached to a human subject for measurement of movement of the human subject; and a mobile communication device coupled to the sensors (by a wireless personal area network or cables, for example) and configured to receive data from the sensors, the mobile device comprising: (1) a display unit; (2) an input unit; (3) an evaluation subsystem for evaluating balance capabilities of a human subject utilizing data collected when the human subject is performing one or more balance evaluation exercises, the data including data received from the sensors; (4) an expert subsystem for prescribing an exercise plan; and (5) a training subsystem for maintaining an exercise plan including one or more balance training exercises for the human subject; wherein the exercise plan is determined by at least one of a balance evaluation by the evaluation subsystem, performance data provided by the training subsystem, and input from a health professional; wherein the sensors are configured to measure movement of the human subject during performance of one or more of an evaluation exercise and a training exercise; and wherein the evaluation subsystem is configured to calculate gait parameters of the human subject from data collected from the sensors. The system may further comprise a remote subsystem on a remote server coupled to the mobile device by a wide area network, the remote subsystem being configured to receive data from the mobile device and send software updates to the mobile device for at least one of the evaluation subsystem, the expert subsystem and the training subsystem. The system may further comprise a remote interface coupled to the mobile device by a wide area network, the remote interface being configured to permit one or more of monitoring the performance of the human subject and controlling the evaluation and training of the human subject. The mobile device may further comprise an incentive subsystem for providing motivational messages to the human subject on the display unit of the mobile device. Furthermore, the sensors may include sensors attached by bands to various parts of the human subject, such as ankles and upper body (trunk, including lower back and chest), and/or sensors provided in the mobile communication device, such as a smart phone.

According to some embodiments, a method of evaluating and training human balance may comprise: providing a mobile communication device comprising: (1) sensors; (2) a display unit; (3) an input unit; (4) an evaluation subsystem for evaluating balance capabilities of a human subject utilizing data collected when the human subject is performing one or more balance evaluation exercises, the data including data received from the sensors; (5) an expert subsystem for prescribing an exercise plan; and (6) a training subsystem for maintaining an exercise plan including one or more balance training exercises for the human subject, wherein the exercise plan is determined by at least one of a balance evaluation by the evaluation subsystem, performance data provided by the training subsystem, and input from a health professional; measuring movement of the human subject by the sensors during performance of one or more of an evaluation exercise and a training exercise; determining balance capabilities of the human subject from the measured movement by the sensors by one or more of the evaluation subsystem, the training subsystem and a remote subsystem on a remote server coupled to the mobile device by a wide area network; and determining one of an initial training program or a modified training program by one or more of the expert system and the remote subsystem from the balance capabilities of the human subject. The method may further comprise providing by the mobile device at least one of an auditory stimulus, a visual stimulus and a tactile stimulus to the human subject for providing a cognitive load or cognitive challenge during performance of one or more of the evaluation exercises and the training exercises. The method may further comprise providing motivational messages to the human subject on the display unit of the mobile device wherein the mobile device further comprises an incentive subsystem for generating the motivational messages. The method may further comprise, before evaluating balance capabilities, collecting information from the human subject regarding self-reported age, physical activity level and level of confidence regarding ability to maintain balance during physical activity, assessing using the information by the evaluation subsystem of a risk of falling of the human subject during balance evaluation exercises, and when the risk is above a threshold providing a warning by the mobile device to the human subject to have a human companion available to provide for the safety of the human subject. The method may further comprise calculating gait parameters of the human subject from data collected from the sensors during performance of the one or more balance evaluation exercises and balance training exercises by the human subject, the calculating being by one or more of the evaluation subsystem, the training subsystem and a remote subsystem on a remote server coupled to the mobile device by a wide area network.

According to some embodiments, a method of evaluating and training human balance may comprise: attaching sensors to a human subject for measurement of movement of the human subject; and providing a mobile communication device coupled to the sensors (by a wireless personal area network or cables, for example) and configured to receive data from the sensors, the mobile device having: (1) a display unit, (2) an input unit; (3) an evaluation subsystem for evaluating balance capabilities of a human subject utilizing data collected when the human subject is performing one or more balance evaluation exercises, the data including data received from the sensors; (4) an expert subsystem for prescribing an exercise plan; and (5) a training subsystem for maintaining an exercise plan including one or more balance training exercises for the human subject, wherein the exercise plan is determined by at least one of a balance evaluation by the evaluation subsystem, performance data provided by the training subsystem, and input from a health professional; providing instructions to the human subject by the mobile device for performing one or more balance evaluation exercises and balance training exercises; measuring movement of said human subject by said sensors during performance of said one or more of an evaluation exercise and a training exercise; determining balance capabilities of the human subject from the measured movement by the sensors by one or more of the evaluation subsystem, the training subsystem and a remote subsystem on a remote server coupled to the mobile device by a wide area network; and determining one of an initial training program or a modified training program by one or more of the expert subsystem and the remote subsystem from the balance capabilities of the human subject. The method may further comprise, calculating gait parameters of the human subject from data collected from the sensors during performance of the one or more balance evaluation exercises and balance training exercises by the human subject, the calculating being by one or more of the evaluation subsystem, the training subsystem and the remote subsystem; and may further comprise determining one of the initial training program or the modified training program for the human subject using as input data at least the gait parameters of the human subject. The method may further comprise providing by the mobile device at least one of an auditory stimulus, a visual stimulus and a tactile stimulus to the human subject for providing a cognitive load or cognitive challenge during performance of one or more of the evaluation exercises and the training exercises. The method may further comprise providing motivational messages to the human subject on the display unit of the mobile device wherein the mobile device further comprises an incentive subsystem for generating the motivational messages. The method may further comprise, before evaluating balance capabilities, collecting information from the human subject regarding self-reported age, physical activity level and level of confidence regarding ability to maintain balance during physical activity, assessing using the information by the evaluation subsystem of a risk of falling of the human subject during balance evaluation exercises, and when the risk is above a threshold providing a warning by the mobile device to the human subject to have a human companion available to provide for the safety of the human subject.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

DETAILED DESCRIPTION

Embodiments of the present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements. Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The present invention addresses the improvement of human balance using medical science implemented using mobile and/or wearable technology. In embodiments, a mobile app (a small, specialized program downloaded onto a mobile device) plus wearable sensors plus an online service allow people on their own to evaluate their balance capabilities, and then do training exercises specifically designed to improve their balance.

Figure 1:
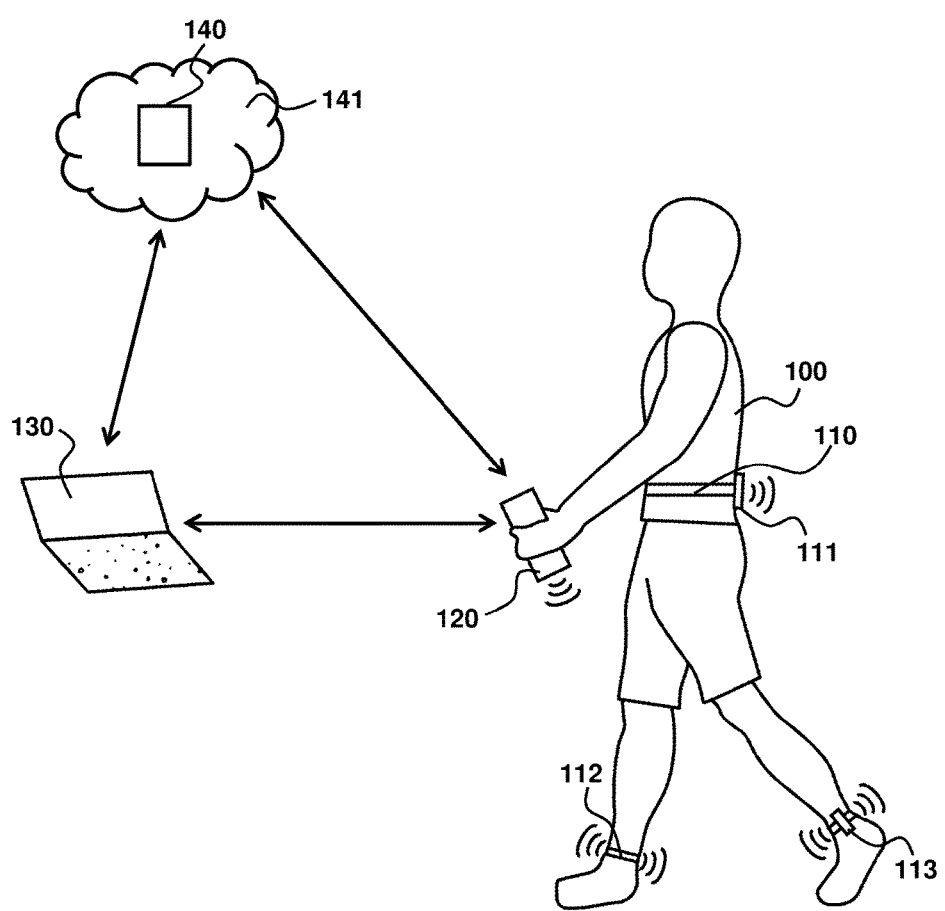
FIG. 1 is a schematic representation of a human subject interacting with a human balance testing and training system, according to some embodiments of the present invention.

An embodiment of a system for evaluating and improving human balance is shown in FIG. 1. The system comprises: an upper body sensor 111 and ankle sensors 113 (one fixed to each ankle, typically on the outside of the ankle at the ankle bone) attached to a human subject 100 by an upper body band 110 and ankle bands 112, respectively; a mobile communication device 120, such as a smartphone, which may be hand held, as shown, or fixed to the human subject by a suitable band or item of clothing; a remote interface 130; and a remote server 140 situated in the Cloud 141. Two-way wide area network (WAN) communication, for example the Internet, is indicated between the mobile communication device, the remote interface and the remote server. Wireless personal area network communication, such as Bluetooth communication, is indicated between the mobile communication device and the sensors 111, 113. (In some embodiments, the coupling between the sensors and the mobile communication device may be by cables, instead of the wireless coupling.) The upper body sensor 111 may be attached by the band 110 to the lower back, as shown, to the chest, or some other part of the trunk of the human subject. The mobile communication device will typically have sensors built-in, which can also be used to determine movement of the human subject, as described in more detail below. The remote interface 130 may be accessed by a healthcare professional, family or friend, as discussed in more detail below. The remote server 140 in the Cloud provides processing, data storage, software upgrade services, etc. to the system through the Internet.

In embodiments a system for evaluating and improving human balance includes the following three basic elements: the sensors for detecting movement of the human subject, a mobile app loaded and operating on a processor in the mobile communications device held by or attached to the human subject, and an on-line service (OLS)—provided by the remote server.

The sensors utilize various combinations of 3-axis gyroscopes, 3-axis accelerometers and 3-axis magnetometers to measure the movement of the human subject. The sensors are mounted such that they can measure the subject's movements with sufficient accuracy to determine the key parameters of the subject's gait. Two typical locations for affixing sensors to the subject are near the ankle bone and at the lower back near the L4 vertebrae of the spine, although other locations can also be used. (Ankle sensor bands are constructed specifically to locate the sensor unit near the point of the ankle bone, in order that the readings from the sensors can lead to a more accurate determination of gait cadence, stride length, foot height, and gait speed.) The key gait parameters include: stride length, stride width, foot height, cadence (i.e. the timing of each step), and the variability of the previous 4 parameters. The sensors communicate the movement data or the gait parameters to the mobile app via a low power communication link such as BluetoothLE. The sensors are battery powered, so give excellent autonomy to the human subject. In certain circumstances multiple sensors are placed at the same location and combine the measurement signals to reduce noise and improve the overall accuracy of the measurement. Furthermore, in some embodiments the gait parameters may be derived by attaching the mobile communications device (with internal sensors) to the lower back of the human subject or other location on the body. The gait parameters (i.e. cadence, stride length, foot height, foot width, etc.) are derived through signal processing of the gyroscope and accelerometer signals. This signal processing includes various of filtering, threshold detection, and integration steps, which signal processing is standard for calculating movement based on this sort of accelerometer/gyro sensor and known to those skilled in the art. However, improvements have been made over the prior art methods, which led to the derivation of a new derivation process as described below.

Derivation of gait parameters may in embodiments proceed as follows. Note that at the beginning of every walking test the subject is asked to stand still for an initial 5 seconds so that the sensor data can be oriented and normalized.

(1) Load and validate sensor data: (a) load the accelerometer and gyroscope data; (b) ensure the timestamps are correct; (c) ensure the accelerometer and gyroscope have the right units.

(2) Correct for sensor orientation—this step is essential in the case where a sensor is placed on the ankle upside down or even at a slightly different angle to the vertical—as follows: (a) identify the initial gravity vector using the first 5 seconds of accelerometer data; (b) use the calculated vector to rotate both accelerometer and gyroscope data (the whole dataset) so that the gravity vector points downwards; (c) renormalize the accelerometer data so that the magnitude during the first 5 seconds is 1 g.

(3) Identify steps based on the mid-stance point of the walk cycle and timing/cadence: (a) multiply the magnitude of the accelerometer and gyroscope signals to get a "motion signal" (b) detect the time periods without movement (below a threshold); (c) smooth these time periods using a series of morphological dilation and erosion processes; (d) select the midpoint in each stationary time period; (e) the time between midpoints gives the timing/cadence of each step.

(4) Remove gravity bias from accelerometer data during the walk: (a) estimate the rotation of the sensor at each time frame over the whole signal using AHRS (attitude and heading reference system); (b) multiply the initial gravity vector (pointing downwards) by the sensor rotation at each time frame; (c) remove estimated gravity from accelerometer data.

(5) Segment the accelerometer and gyroscope data into chunks for each step.

(6) Estimate step length, foot height and step width by the following process applied to each step: (a) integrate acceleration to get velocity vector; (b) remove drift from velocity data (i.e. the velocity must start and end at 0 at each step); (c) integrate velocity to get position; (d) remove bias from position data (shift data if there are any negative values); and (e) calculate stride length by subtracting the position in the first and last frames.

7) Variability and asymmetry: the data from step 3e and 6e can then be used to calculate the step variability, the irregularity and asymmetries between the two legs etc.

Furthermore, the gait data and calculated parameters collected for a particular subject may undergo further analysis using detrended fluctuation analysis (DFA) and approximate entropy analysis (ApEn). These techniques are useful for providing more in-depth analysis of the regularity, unpredictability, and self-similarity of time series data such as the physiological data described herein.

Furthermore, sensors may be used to measure and monitor walk speed variations for a human subject. Sensors (accelerometer and gyroscope) are used to measure movement during walking. These signals are processed, by the mobile app or remote server, for example, to determine a subject's overall average speed of walking. (Note that walking speed may also be measured by more direct measurement of walking time and distance). A subject's average walking speed is measured at intervals, e.g. weekly, to identify trends in gait speed. The system processes the data and identifies any rapid changes in gait speed which is an indicator of increased risk of falling. This information is communicated back to the subject and, if permissions are set, to external people such as user's family, caregiver, doctor, etc.

Furthermore, the internal sensors in the mobile communication device (accelerometers and gyroscopes) may be programmed to automatically count the number of "stand-ups" a user can complete in a given time. Counting the number of standups a human subject can perform in a period of time is useful as a measure of the strength the subject has in their legs.

The mobile app has many functions, detailed as follows. (1) The app communicates with the sensors over a low power communication link in order to receive the gait parameters or the movement data. (2) The app does further analysis of the received sensor data to get full gait parameters (or transfers the data to the remote server for further analysis and receives from the remote server the gait parameters). (3) The app uses the sensors of the smartphone when the human subject is doing certain exercises. These readings give a measurement of how much the person is moving during the exercise. (4) The app on the smartphone provides a user interface to the user, through the screen (display unit), touch input (an example of an input unit), audio, and tactile/haptic feedback. The app determines the correct test and sequence of tests to give to the subject, based on the responses given by the subject to certain questions, as well as the results of the evaluation tests. A series of questions are asked, for example, the age, self-reported activity level and the self-reported balance level for the subject. Then, depending on the answers to these questions, the app determines what sort of stability test the subject should start with. For example, an elderly person who is normally sedentary and is not too confident of their balance would be asked to stand on two feet for 20 seconds as their stability is measured by the system. On the other hand, a person who is under 50, very active and feels good about their balance would start at a much harder level, perhaps standing on one foot with their eyes open for 20 seconds. In every case, if a person performs very well on such a stability test, the subject is assigned to a harder test (e.g. if the subject can stand for 20 seconds on one foot with eyes open, the subject may be assigned 20 seconds on one foot with eyes closed). If the subject does very poorly, i.e. the subject cannot even maintain the given position for 3 seconds, the subject is assigned an easier test. (6) The app determines the correct training exercises to assign, and keeps track of progress on the training program. When a subject starts training, the app may set the initial training level based on the results of a Balance Index test. A series of training levels, e.g. Bronze, Silver, Gold, etc. have been implemented to make this easier to understand and to give users motivation to progress up to the next level. The "training level" specifies which exercises the subject does each day, and the target for how long they should do each exercise. As the subject does their exercises each day the app monitors their progress against these targets. When the subject is able to do sufficiently well against all their targets, the subject is offered the chance to be "promoted" up to the next level. Note that the training program may also be determined by algorithms on the remote server in the cloud. For example, when a subject is newly promoted to a level (e.g. Silver from Bronze), the app will set the targets for all the exercises to be somewhat easier than would be normal. This is done so that the subject can have some successful initial sessions at the new level, and will maintain their motivation to continue. Similarly, if their score on a particular exercise is not good but they are doing well on all other exercises at that level, that may still be sufficient for being offered promotion to a higher level. (7) The app provides "dual task training" by actively engaging the subject's mind while they are simultaneously doing physical exercises. This dual-task approach has been shown in research to be a highly effective way to improve balance, as well as delay onset of memory loss, dementia, Parkinson's, and other degenerative diseases. The dual tasks can range in difficulty from answering simple questions, to color based or location based quiz questions, to interactive games. (8) The app communicates via the Internet to an online service to upload results, download analyses and updates, and enable communication with family and medical care givers.

Figure 2:
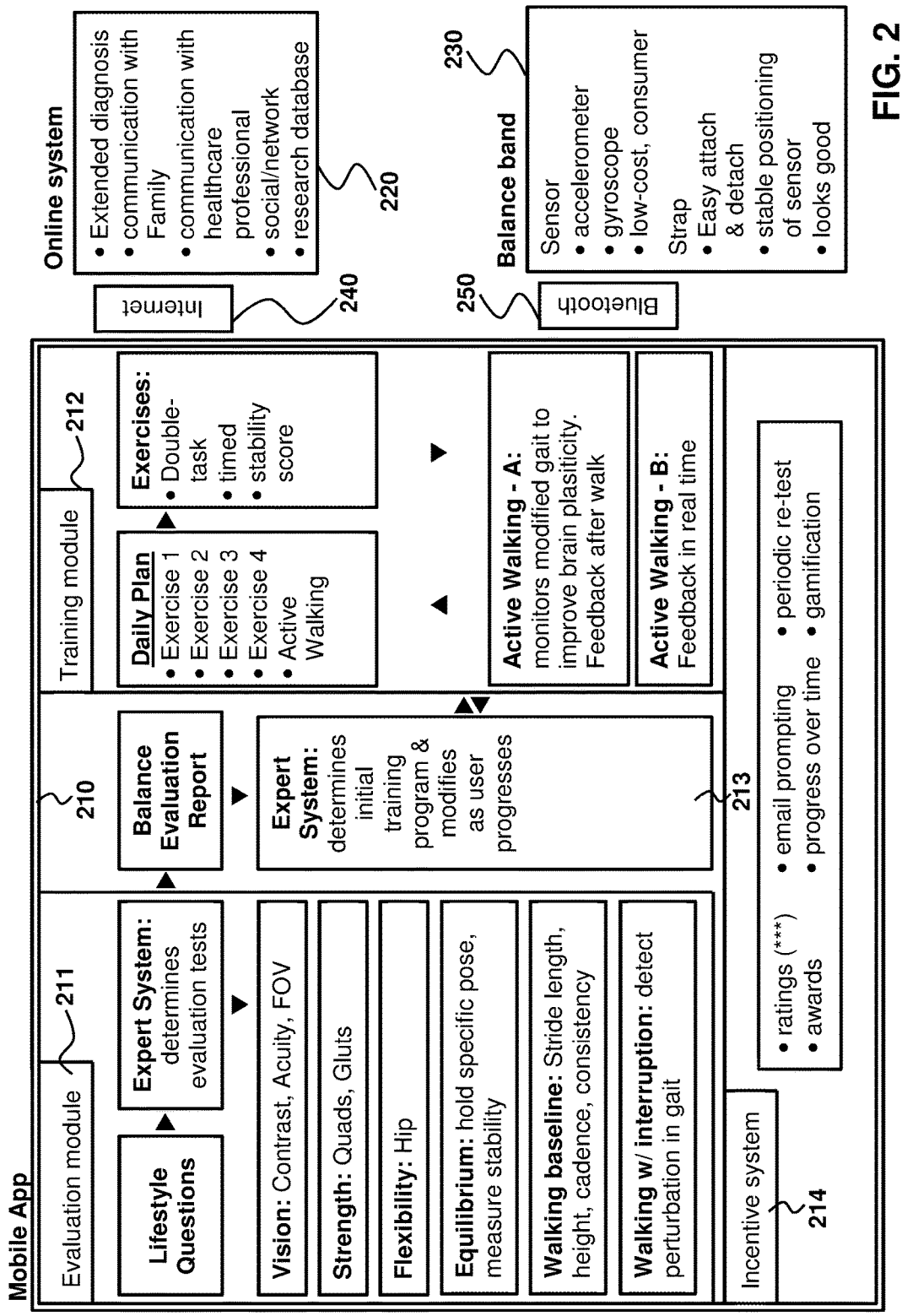
FIG. 2 is a schematic representation of various subsystems/modules of a human balance testing and training system, according to some embodiments of the present invention.

FIG. 2 shows a schematic representation of the mobile app 210 on the mobile communications device, and connected devices. The mobile app includes various subsystems including an evaluation subsystem 211, a training subsystem 212, an expert subsystem 213 and an incentive subsystem 214. (The expert subsystem, which determines the initial training program and modifies the program as the user progresses, is considered to be part of the training subsystem in the description provided below.) Connection to an OLS 220 (on the remote server) via the Internet 240 is shown, and connection to sensors 230, including sensors on straps, via a wireless personal area network 250, such as Bluetooth, is also shown. (The sensors mounted on straps are referred to as balance bands.) The training module includes active walking exercises for which feedback is provided to the user after completion, or in other embodiments in real time while walking, as described in more detail below.

Furthermore, the evaluation subsystem of the mobile app may provide to the subject a special "safety gate" screen on the mobile communication device (also on the remote interface, if permissions are given) to tell the subject who may be more at risk of falling during evaluation or training to be sure to have someone with them while they do the set exercises. The provision of this "safety gate" is based on factors such as the subject's self-reported age, activity and feeling about their balance.

Furthermore, the evaluation subsystem of the mobile app may vary the sensitivity of the "shake threshold" depending on the level of difficulty of the evaluation exercise. The "shake threshold" is the limit of the amount of liberation, as measured by the sensors (mobile communication device sensors and/or band mounted sensors), that has to be reached before the app will automatically cut off the evaluation exercise. This is important for accurately measuring the ability to remain stable, and also for insuring the safety of the subject.

The training subsystem, which also includes the expert subsystem, is an engine that looks at the scores the human subject made on the evaluation, and based on a set of internal rules determines which exercises they should do, and for how long they should do each one. When a person starts training, the app sets their initial training level based on the results of the Balance Index test. (A series of training levels, e.g. Bronze, Silver, Gold, etc. have been implemented to make the training process easier to understand for the subject and to give human subjects motivation to progress up to the next level.) The "training level" specifies which exercises they do each day, and the target for how long they should do each exercise. As a subject does their exercises each day the app monitors their progress against these targets. When they are able to do sufficiently well against all the targets, they are offered the chance to be "promoted" up to the next level. Note that the training program is also determined by analytical programs run on the remote server in the Cloud. For example, when a person is promoted to a new level (e.g. they are now Silver whereas before they were Bronze), the expert system will set the targets for all the exercises to be somewhat easier than would be normal. This is so that the subject can have some successful initial sessions at the new level, and will maintain their motivation. Similarly, if their score on a particular exercise is not good whereas they are doing well on all other exercises at that level, that may still be sufficient for being offered promotion to a following level.

The OLS receives information from the mobile communications device, and performs several key functions, described as follows. (1) The OLS keeps track of the progress and scores of each human subject. This is for further analysis of their individual data and for the determination of appropriate training programs, as well as for analysis of data across a large population. (2) The OLS manages communication with external parties, such as family members, friends, and/or healthcare workers. An appropriate level of security is included for each of these. (3) The OLS provides links to social networks so the subject can communicate their progress or scores to a wider audience. (4) The OLS will also download updates to the contents of the app, for example additional questions for the dual task training.

A "Balance Index" is used herein—it is intended to give a numerical way to measure and compare balance capabilities. Three basic levels are defined which combine to make up the full Balance Index.

Static Balance—this is a person's ability to be stable when standing still. It does not emphasize movement. Static Balance index is calculated as a combination of three factors which are measured by the app during a Balance evaluation. The 3 factors are: a) Stability score—based on which standing positions they were able to maintain, for how long, and with what degree of shaking/steadiness; b) Strength score—based on how many "standups" they could do in a 20 second period (a "standup" means standing up and sitting back down again from a chair, without using your hands or arms); c) Movement score—based on time it takes to do the following: i) start from sitting position; ii) stand up without using hands or arms; iii) walk 3 meters; iv) turn around, walk 3 meters back to the chair; and v) turn around and sit back down.

Dynamic Balance—this is a person's basic balance capability when moving. It is measured also by the variance in the gait parameters. Dynamic Balance is measured directly as the variability (usually expressed as a percentage) in stride length, foot height, and cadence. An additional number represents the variability or difference between the two legs.

Cognitive Balance—this is the amount of balance degradation that happens when a person needs to focus their attention away from the balance task. It is measured by seeing the change in the Dynamic Balance when a person is walking and their attention is interrupted. Cognitive Balance is directly measured as the increase in Dynamic Balance variability that is caused by adding a cognitive load or cognitive challenge, e.g. asking a question to the person while they are walking.

Both the Cognitive Balance and the Dynamic Balance are typically measured using balance bands, although in some embodiments the built-in sensors in the mobile communication device may also be used to measure these levels of the Balance Index. The Static Balance may be measured without balance bands, using the sensors in the mobile communication device, for example.

Furthermore, some embodiments of the systems and methods of the present invention include a remote interface—as shown in FIG. 1, for example. The remote interface may be a web or mobile interface. The remote interface may give a medical professional access to, and sometimes control over, the evaluation and training program and data for a specific human subject, or for multiple users. Examples of these medical professionals include: an exercise trainer at a retirement home, a balance class coach, a physiotherapist, a medical doctor, etc. Access to a subject's data would only be allowed after explicit permission from the subject. The medical professional would be able to access and see historical data on a subject's evaluation and training, and have access to even more detailed information such as the raw scores, the raw vibration information, etc. The medical professional would also be able to block certain exercises from being assigned, if appropriate. For example, if the medical professional had examined the subject and diagnosed knee problems, the medical professional might block the system from assigning a long lunge exercise. The medical professional could also specify, through the remote interface, a certain set of exercises that will be assigned to the subject. In other words the medical professional can predefine what exercises the app gives to the subject so the subject has a program customized by the medical professional. Further examples of the use of the systems and methods of the present invention include: (1) accessing by an instructor the balance data collected on class participants during a balance class for providing feedback to the class participants regarding their performance and/or progress with balance evaluation and/or balance training; (2) accessing balance data collected on residents at a retirement home by a medical professional to screen the residents for balance issues.

Furthermore, some embodiments of the systems and methods of the present invention include a remote server in the Cloud—as shown in FIG. 1, for example. In some embodiments, the training subsystem sends the results of each training session to the cloud at the end of the training session. Analysis of the training data is done in the cloud, so it can be much more extensive than a mobile communication device based system, and it can also be modified and upgraded much more easily. A new training program, including which exercises, how long, and what sort of Double Tasking, is sent back to the mobile communication device. Also engagement messages are determined by the remote server and sent to the mobile communication device for display to the human subject, to help keep them more engaged with the training process. Use of "engagement messages" is one of the means that is used to keep the subject interested and motivated to continue with the training program. These messages can come in a wide variety of forms. For example: every day the subject can be reminded on the mobile communication device to do their exercises at a certain time if they have not done them yet; when a subject completes an exercise and reaches the target for that exercise, a special message of congratulations is shown on the display of the mobile communication device; if a subject tries all the exercises for the day, regardless of how well they do, a message of encouragement is shown; if a user has not done the training exercises for two days, on the third day the subject is sent a message to remind them to continue with the training program; at various intervals the subject may be sent messages emphasizing the importance of maintaining good balance to lead an active lifestyle. Furthermore, new exercises can be downloaded from the Cloud to the training subsystem to increase the variety in the app. Each new exercise will include at a minimum a thumbnail image of the exercise, an animation of doing the exercise, and explanation texts for the human subject to view on the display unit of the mobile communications device. Furthermore, new types of Double Tasking (DT) exercises may also be downloaded from the Cloud. This may include new categories for existing DT exercises (e.g. new categories for the "find the one that doesn't fit" exercise), or completely new types of DT exercises.

Note that if there is no internet connection such that a new exercise program cannot be downloaded from the remote server, the exercise program last used can be used again— the app can work with or without an Internet connection. Furthermore, data ready to be uploaded to the remote server may be stored on the mobile communications device until Internet connect is reestablished, then all new training data is uploaded to the Cloud.

Furthermore, in some embodiments the app will use a simple rating system to ask how the human subject feels at the end of each exercise session and sometimes at the beginning of each exercise session, and will use this additional information when determining the next exercise programs.

Furthermore, in some embodiments graphically based video games may be used as a Double Tasking cognitive task to improve the effect of balance training. This is in addition to the other cognitive tasks such as answering questions, matching shapes, doing math problems, etc.

Example 1: Basic Operation of the Evaluation Subsystem

The evaluation subsystem in embodiments may operate as follows:
1. The person (human subject) provides some personal information to the app such as age, activity level, current feeling of balance.
2. This information is used by the app (evaluation subsystem) to determine what balance stability evaluation test level to start with. For example, if the person is young and active, the first evaluation test might be to stand on one leg. If the person is quite elderly and not active, the first evaluation test might be to stand on 2 feet with the feet close together.
3. The person stands in the assigned evaluation position for as long as they can, up to 20 seconds. The smartphone uses the internal accelerometers to measure stability. Sensor bands may also be used to measure stability.
4. Based on the person's score, the app determines if they should be assigned a harder evaluation test, a simpler evaluation test, or if the stability evaluation is complete.
5. The app takes the person through a simple evaluation of strength of the leg quadriceps and glutes (muscles of the buttocks).
6. The app takes the person through a "Timed Up and Go Test". This test requires the person to stand up from a sitting position, walk 3 meters, turn around, walk back, turn around, and sit back down again.
7. The app does an evaluation of the person's vision capabilities, as vision is also very important for maintaining a sense of balance. As an example, some basic vision tests such as visual acuity (clarity of vision), and contrast sensitivity can be done using the display unit on the mobile communication device. Note that if the person's vision test results are below a set threshold a consultation with a vision specialist is recommended to the subject as this may have a strong impact on their balance capability.
8. The person is asked to take a short walk while wearing the balance bands. During the walk the measurement data from the balance bands is sent to the app.
9. The person is asked to do a second walk while wearing the balance bands. During this second walk, they must periodically respond to questions asked by the mobile app. The bands measure the variation in stride parameters caused by the requirement to answer questions.
10. Based on all of the information collected, the app determines the person's Balance Index.

Example 2: Basic Operation of the Training Subsystem

The training subsystem in embodiments may operate as follows:
1. The app uses all the data collected in the evaluation to determine the best training exercises for the person. A training schedule is established for 4 to 6 weeks. Training is intended to take place for 5 minutes each day.
2. Each day, the app shows the training exercises to be done that day. As the person accomplishes each exercise, the app indicates the ones that are left. When they are all done, it shows that the day's training is completed. It also gives feedback on how well the exercises were accomplished.
3. A typical training exercise would tell the person to take a particular stability position (e.g. feet tandem with eyes closed or on one foot with eyes open.) They are instructed to hold that position for a specified period of time. While they are holding the position, they also are asked to respond to a series of questions or puzzles or riddles. This is to engage the brain separately from the effort of holding the physical position. Examples of these questions might be: "What is the capital of France?"; "Which one does not belong: hat, dog, shoe?"; "What is 27 minus 19?" The accelerometers in the smartphone and the balance bands are used to collect information as to how stable the person is while they are doing the training exercise.
4. For certain people, they are instructed to take a short walk using a unique "Controlled Walk" technique. This requires that they actively, consciously control the tempo of the walk, and try to stretch each step slightly. The intent again is that the brain has to be fully involved. During the Controlled Walk movement data is collected by sensors attached to the subject by balance bands or via sensors in the mobile communication device (worn by subject, attached to subject by a band, held by subject, etc.) in order to determine the key gait parameters in real-time or near real time. This is to evaluate if the person was correctly doing Controlled Walk, and also to provide feedback to them to help them maintain the Controlled Walk approach.
5. Based on the results of the various training exercises, the app will dynamically assign more difficult or easier exercises as appropriate.
6. Throughout the training period, the app will give awards, recognition, prizes, etc., to aid as an incentive to keep the person following the program. The app may also send reminder messages (e.g. email, text, phone alarms, etc.) to remind the person to do their training exercise.
7. After the completion of the scheduled exercise program, the app instructs the person to take another evaluation test to check on their progress.

Example 3: Balance Evaluation and Training for an Elderly Person

Below is an example of what the evaluation test and training exercises might involve for an older person. Note this example is illustrative, not comprehensive.
Evaluation:
1. Stand with two feet close together, eyes closed, arms out straight. Hold this position for 20 seconds, while stability is being measured. If they do well, they go to #2.
2. Stand with feet in "Tandem" position (heel to toe), eyes open, and arms out straight. Hold this position for 20 seconds while stability is being measured. If they do well, they go to #3.
3. Stand on one foot with eyes open and arms out straight. Attempt to hold this position for 20 seconds while stability is being measured.
4. Begin by sitting in a chair with no arms. Stand up and then sit down repeatedly, doing as many repetitions as possible within a 20 second window.
5. Walk for 30 seconds. The system measures movement to calculate stride length, stride width, foot height, cadence (i.e. the timing of each step), the variability of these 4 parameters and any asymmetries between left and right.
6. Do a second 30 second walk, this time with the mobile app asking occasional questions.
Again, the system measures movement to calculate stride length, stride width, foot height, cadence (i.e. the timing of each step), and the variability of these 4 parameters, specifically to measure the impact of the questions.
Training:
1. Stand with feet in "Tandem" position (heel to toe), eyes open, arms out straight and holding the smartphone (mobile communication device). Attempt to maintain this position for 30 seconds while simultaneously answering a series of questions on the smartphone (e.g. What is the capital of France?; What is 27 minus 19?).
2. Stand on one foot with eyes open, arms out straight and holding the smartphone. Attempt to maintain this position for 30 seconds while simultaneously solving a set of puzzles on the smartphone (e.g. which shape is not like the others; a memory game which requires that you remember where blue dots are located, etc.).
3. Place the back against the wall, and slide down until the thighs are horizontal and the shank (part of the leg from the knee to the ankle) is vertical. Maintain this position for a set period of time (depending on how well the subject scored on the stand up test, and how well they have done on previous Wall Sit exercises).
4. Walk for 10 minutes using the "Controlled Walk" technique. This requires that the person actively, consciously control the tempo of each step, and try to stretch each step slightly. During the Controlled Walk movement data is collected by sensors attached to the subject by balance bands or via sensors in the mobile communication device (worn by subject, attached to subject by a band, held by subject, for example) in order to measure the key gait parameters in real-time or near real time. This is to evaluate if the person is correctly doing the Controlled Walk. The system also provides feedback to the subject to help them maintain the Controlled Walk approach. The intent is that the brain has to be fully involved and controlling the walking activity.

Example 4: Balance Evaluation and Training for a Younger Person

Below is an example of what the evaluation test and training exercises might involve for a younger person. Note this example is illustrative, not comprehensive.
Evaluation:
1. Stand on one foot with eyes open, arms out straight. Hold this position for 20 seconds, while stability is being measured. If they do well, they go to #2.
2. Stand on one foot with eyes closed, arms out straight. Hold this position for 20 seconds, while stability is being measured. If they do well, they go to #3.
3. Stand on one foot with eyes closed, arms out straight. Begin counting backwards from 100 by 3's. Try to hold this position for 30 seconds, while stability is being measured.
4. Begin by sitting in a chair with no arms. Stand up and then sit down repeatedly, doing as many repetitions as possible within a 20 second window.

5. Walk for 30 seconds. The system measures movement to calculate stride length, stride width, foot height, cadence (i.e. the timing of each step), and the variability of these 4 parameters.
6. Do a second 30 second walk, this time with the mobile app asking occasional questions.

Again, the system measures movement to calculate stride length, stride width, foot height, cadence (i.e. the timing of each step), and the variability of these 4 parameters, specifically to measure the impact of the questions.

Training:
1. Stand on one foot with eyes open, arms out straight, holding the smartphone. Attempt to maintain this position for 30 seconds while simultaneously solving a rapid set of puzzles on the smartphone (e.g. which shape is not like the others; a memory game which requires that you remember where blue dots are located, etc.).
2. Stand on one foot with eyes closed, arms out straight, holding the smartphone. Attempt to maintain this position for 60 seconds while simultaneously solving a rapid set of puzzles on the smartphone based on audio and/or haptic stimulus (e.g. touch the left side of the screen if the audio clues are even-numbered, right side if odd-numbered, etc.).
3. Stand on one foot with eyes open, arms out straight, holding the smartphone. Attempt to maintain this position for 60 seconds while simultaneously playing a video game on the smartphone, where the game involves manipulating objects in relation to a moving background frame of reference.
4. Stand on one foot with eyes open, wearing an immersive virtual reality (VR) headset (e.g. Oculus Rift or Samsung Gear VR). Interact with the VR world while maintaining balance on one foot.
5. Place the back against the wall, and slide down until the thighs are horizontal and the shank is vertical. Maintain this position for a set period of time (depending on how well the subject scored on the stand up test, and how well they have done on previous Wall Sit exercises).

The utility of some embodiments of the systems and methods of the present invention for addressing the problem of declining balance in the larger population at a lower cost than currently available clinical approaches, is shown by the following: (1) the system is designed to be inexpensive, utilizing inexpensive sensors and a smartphone, for example; (2) there may be no requirement for a doctor or clinician's time as the system can independently evaluate balance, recommend a training program, and follow up on the accomplishment of that program; (3) the system is very convenient for the human subject and permits self-managed healthcare since the human subject can do the evaluation and training anytime as they do not need to schedule any appointments, they can do the evaluation and training anywhere since they do not need to travel to a particular location, and doing exercise in the privacy of one's home is very attractive to many people; (4) due to the minimal resources required, a balance improvement program can affordably be carried on for a long time; (5) the online nature of the system facilitates sharing and communication and connections between the human subjects and their friends, family and healthcare providers.

Although the present invention has been particularly described with reference to certain embodiments thereof, it should be readily apparent to those of ordinary skill in the art that changes and modifications in the form and details may be made without departing from the spirit and scope of the invention.

What is claimed is:
1. A human balance testing and training system comprising:
   a mobile communication device comprising:
      a computer processor:
      a system memory;
      a network interface comprising one or more communication modules adapted to communicate over a wide area network;
      a combination of sensors for measuring movement and rotation of the mobile communication device, the combination of sensors including (i) a 3-axis gyroscope adapted for measuring orientation and angular velocity and (ii) a 3-axis accelerometer adapted for measuring acceleration, the combination of sensors configured to measure sensor data characterizing movement of a human subject, the sensor data comprising one or more of gyroscope data and accelerometer data;
      a display unit;
      a mobile application operating on the mobile communication device, the mobile application including a balance evaluation subsystem for evaluating balance capabilities of the human subject utilizing data collected when said human subject is performing one or more balance evaluation exercises, said data including data received from one or more of the human subject's interaction with the mobile communication device and said combination of sensors, the balance evaluation subsystem configured to evaluate the data and to provide a balance evaluation for the human subject;
   the mobile application further including an expert subsystem for prescribing an exercise plan for the human subject based on the balance evaluation provided by the balance evaluation subsystem, the exercise plan comprising one or more balance training exercises specifically tailored for improving balance of the human subject; and
   the mobile application further including a training subsystem for administering the prescribed exercise plan received from the expert subsystem to the human subject, the prescribed exercise plan administered as an interactive exercise plan including one or more balance training exercises for said human subject, wherein the training subsystem is configured to collect performance data for the human subject while the human subject is performing the one or more balance training exercises;
   wherein said expert subsystem is adapted to modify the interactive exercise plan as the human subject progresses in accordance with a level of performance of the human subject based on evaluating the performance data for the human subject provided by the training subsystem, wherein updates to the interactive exercise plan are determined based on at least one of the balance evaluation provided by said balance evaluation subsystem, the performance data provided by said training subsystem, and input from the human subject,
   wherein the mobile application is further configured to provide one or more cognitive challenges for dual tasking to actively engage the human subject's mind during performance of one or more balance evaluation exercises and balance training exercises, including (i) communicating the one or more cognitive challenges to the human subject during performance of one or more balance evaluation exercises and balance training exer- cises and receiving performance data while the human subject is under the cognitive challenge, (ii) determining differences in the performance data for the human subject under the cognitive challenge with performance data under conditions without the cognitive challenge, and (iii) evaluating the determined differences in the performance data to ascertain an amount of variability in the human subject's performance during times when the human subject's attention is focused away from performing the balance evaluation or training exercises by the cognitive challenge, and wherein the human balance testing and training system enables the human subject using a mobile communication device to evaluate balance and to receive one or more exercise plans tailored for improving balance of the human subject to reduce risk of falls.

2. The system of claim 1, wherein the combination of sensors is configured to measure movement of the human subject during performance of one or more of the balance evaluation exercises and balance training exercises, the balance evaluation subsystem configured to perform operations comprising:

loading and validating the sensor data comprising the gyroscope data and the accelerometer data;

correcting for orientation of the sensors;

determining cadence of the human subject's gait, including (i) calculating a motion signal based on the accelerometer data and the gyroscope data (ii) detecting stationary time periods wherein the motion signal falls below a threshold value (iii) selecting a midpoint in each stationary time period and (iv) calculating cadence of each step between midpoints in each stationary time period;

determining gait parameters for the human subject based on computing stride length and step height for each step in the human subject's gait based on the sensor data, including performing integration operations on the accelerometer data to acquire position data and calculating the human subject's stride length and step height based on the position data;

calculating one or more of variability and asymmetry in the human subject's gait based on the stride length, step height and the cadence for each step between midpoints in each stationary time period; and storing the gait parameters and variability and asymmetry thereof in the system memory.

3. The system of claim 1, wherein said mobile communication device is adapted to be hand held by the human subject or adapted to be attached to said human subject during performance of one or more of the balance evaluation exercises and the balance training exercises.

4. The system of claim 2, wherein said mobile device is configured to provide at least one of an auditory stimulus, a visual stimulus and a tactile stimulus to said human subject for providing feedback in real time to the human subject during performance of one or more of said balance evaluation exercises and said balance training exercises, the feedback including one or more of the gait parameters.

5. The system of claim 1, further comprising a remote subsystem on a remote server in communication with the mobile communication device via a wide area network, said remote subsystem being configured to receive data from said mobile communication device and send software updates to said mobile communication device for at least one of said evaluation subsystem, said expert subsystem and said training subsystem.

6. The system of claim 5, wherein said software updates are sent daily and wherein said software updates include updates to said exercise plan.

7. The system of claim 5, wherein said combination of sensors and at least one of said evaluation subsystem, said training subsystem and said remote subsystem, are configured to measure the gait of said human subject based on the gait parameters.

8. The system of claim 1, further comprising a remote interface in communication with the mobile communication device via a wide area network, said remote interface being configured to permit one or more of monitoring the performance of said human subject and controlling evaluation and training of said human subject.

9. The system of claim 1, wherein said mobile communication device further comprises an incentive subsystem for providing motivational messages to said human subject on said display unit of said mobile device.

10. The system of claim 1, wherein said combination of sensors and at least one of said evaluation subsystem and said training subsystem are configured to measure the gait of said human subject.

11. A human balance testing and training system comprising:

a mobile communication device comprising:
    a computer processor:
    a system memory;
    a display unit; and
    a network interface comprising one or more communication modules adapted to communicate over a wide area network;

a combination of sensors, the combination of sensors including (i) a 3-axis gyroscope adapted for measuring orientation and angular velocity and (ii) a 3-axis accelerometer adapted for measuring acceleration, the combination of sensors configured to measure sensor data characterizing movement of a human subject, the sensor data comprising one or more of gyroscope data and the accelerometer data; and a mobile application operating on the mobile communication device in communication with the combination of sensors and configured to receive data from one or more of the human subject's interaction with the mobile communication device and said combination of sensors, the mobile application including a balance evaluation subsystem for evaluating balance capabilities of the human subject utilizing data collected when said human subject is performing one or more balance evaluation exercises, said data including data received from one or more of the human subject's interaction with the mobile communication device and said combination of sensors; the balance evaluation subsystem configured to evaluate the collected data and to provide a balance evaluation for the human subject, wherein the mobile application operating on the mobile communication device further comprises:

an expert subsystem for prescribing an exercise plan for the human subject based on the balance evaluation provided by the balance evaluation subsystem, the exercise plan comprising one or more balance training exercises tailored for improving balance of the human subject; and a training subsystem for administering the prescribed exercise plan received from the expert subsystem to the human subject, the prescribed exercise plan administered as an interactive exercise plan including one or more balance training exercises for the human subject, wherein the training subsystem is configured to collect performance data for the human subject during performance of the one or more balance training exercises, wherein the expert subsystem is adapted to modify the interactive exercise plan as the human subject progresses in accordance with a level of performance of the human subject based on evaluating the performance data for the human subject provided by the training subsystem, wherein the mobile application is further configured to provide one or more cognitive challenges for dual tasking to actively engage the human subject's mind during performance of one or more balance evaluation exercises and balance training exercises, including (i) communicating the one or more cognitive challenges to the human subject during performance of one or more balance evaluation exercises and balance training exercises and receiving performance data while the human subject is under the cognitive challenge, (ii) determining differences in the performance data for the human subject under the cognitive challenge with performance data under conditions without the cognitive challenge, and (iii) evaluating the determined differences in the performance data to ascertain an amount of variability in the human subject's performance during times when the human subject's attention is focused away from performing the balance evaluation or training exercises by the cognitive challenge, and wherein the human balance testing and training system enables the human subject using a mobile communication device to evaluate balance and to receive one or more exercise plans tailored for improving balance of the human subject to reduce risk of falls.

12. The system of claim 11, wherein the mobile communication device is configured to perform operations comprising:

loading and validating the sensor data comprising the gyroscope data and the accelerometer data;

correcting for orientation of the sensors;

determining cadence of the human subject's gait, including (i) calculating a motion signal based on the accelerometer data and the gyroscope data (ii) detecting stationary time periods wherein the motion signal falls below a threshold value (iii) selecting a midpoint in each stationary time period and (iv) calculating cadence of each step between midpoints in each stationary time period;

determining gait parameters for the human subject based on computing stride length and step height for each step in the human subject's gait based on the sensor data, including performing integration operations on the accelerometer data to acquire position data and calculating the human subject's stride length and step height based on the position data;

calculating one or more of variability and asymmetry in the human subject's gait based on the stride length, step height and cadence for each step between midpoints in each stationary time period; and storing the gait parameters and variability and asymmetry thereof in the system memory.

13. The system of claim 11, wherein said gait parameters include any selection of stride length, stride width, foot height, step cadence, walking speed, and measures of variabilities or asymmetries of stride length, stride width, foot height, step cadence and walking speed, wherein said variabilities or asymmetries are a measure of one or more of stride-to-stride variabilities or asymmetries and left-leg-to-right-leg variabilities or asymmetries.

14. The system of claim 11, wherein said mobile communication device is configured to provide at least one of an auditory stimulus, a visual stimulus and a tactile stimulus to said human subject for providing feedback in real time to the human subject during performance of one or more of said balance evaluation exercises and said balance training exercises, the feedback including one or more of the gait parameters.

15. The system of claim 12, further comprising a remote subsystem on a remote server in communication with the mobile communication device via a wide area network, said remote subsystem being configured to receive data from said mobile communication device and send software updates to said mobile communication device for at least one of said evaluation subsystem, said expert subsystem and said training subsystem.

16. The system of claim 15, wherein said software updates are sent daily and wherein said software updates include updates to said exercise plan.

17. The system of claim 15, wherein said remote subsystem is further configured to calculate gait parameters of said human subject from data collected from said combination of sensors.

18. The system of claim 11, further comprising a remote interface in communication with the mobile communication device via a wide area network, said remote interface being configured to permit one or more of monitoring the performance of said human subject and controlling the evaluation and training of said human subject.

19. The system of claim 11, wherein said mobile communication device comprises device sensors configured to measure movement of said human subject during performance of one or more of an evaluation exercise and a training exercise.

20. The system of claim 19, wherein said mobile communication device is adapted to be hand held by said human subject during performance of one or more of an evaluation exercise and a training exercise.

21. The system of claim 19, wherein said mobile communication device is adapted to be attached to said human subject during performance of one or more of an evaluation exercise and a training exercise.

22. The system of claim 19, wherein said sensors include one or more of said device sensors.

23. The system of claim 11, wherein said mobile communication device further comprises an incentive subsystem for providing motivational messages to said human subject on said display unit of said mobile communication device.

24. A method of evaluating and training human balance, comprising:

at a mobile communication device comprising a computer processor, a system memory, a display unit, a network interface comprising one or more communication modules adapted to communicate over a wide area network, and a combination of sensors for measuring movement and rotation of the mobile communication device, the combination of sensors including (i) a 3-axis gyroscope adapted for measuring orientation and angular velocity and (ii) a 3-axis accelerometer adapted for measuring acceleration, the combination of sensors configured to measure sensor data characterizing movement of a human subject, the sensor data comprising one or more of gyroscope data and accelerometer data:

receiving, at a balance evaluation subsystem operating on the mobile communication device for evaluating balance capabilities of a human subject, data collected when said human subject is performing one or more balance evaluation exercises, said data including data received from one or more of the human subject's interactions with the mobile communication device and data received from said combination of sensors, the balance evaluation subsystem configured to evaluate the data and to provide a balance evaluation for the human subject;

prescribing an exercise plan for the human subject, at an expert subsystem, based on the balance evaluation provided by the balance evaluation subsystem, the exercise plan comprising one or more balance training exercises specifically tailored for improving balance of the human subject; and administering, using a training subsystem, the prescribed exercise plan received from the expert subsystem to the human subject, the prescribed exercise plan administered as an interactive exercise plan including one or more balance training exercises for said human subject, wherein said expert subsystem is adapted to modify the interactive exercise plan as the human subject progresses in accordance with a level of performance of the human subject based on evaluating the performance data for the human subject provided by the training subsystem, wherein updates to the interactive exercise plan are determined based on at least one of the balance evaluation provided by said balance evaluation subsystem, the performance data provided by said training subsystem, and input from the human subject;

providing one or more cognitive challenges for dual tasking to actively engage the human subject's mind during performance of one or more balance evaluation exercises and balance training exercises, including (i) communicating the one or more cognitive challenges to the human subject during performance of one or more balance evaluation exercises and balance training exercises and receiving performance data while the human subject is under the cognitive challenge, (ii) determining differences in the performance data for the human subject under the cognitive challenge with performance data under conditions without the cognitive challenge, and (iii) evaluating the determined differences in the performance data to ascertain an amount of variability in the human subject's performance during times when the human subject's attention is focused away from performing the balance evaluation or training exercises by the cognitive challenge, wherein the human balance testing and training system enables the human subject using the mobile communication device to evaluate balance and receive interactive exercise plans tailored for improving balance of the human subject to reduce risk of falls.

25. The method of claim 24, wherein the combination of sensors is configured to measure movement of the human subject during performance of one or more of the balance evaluation exercises and balance training exercises, the balance evaluation subsystem configured to perform operations comprising:

loading and validating the sensor data comprising the gyroscope data and the accelerometer data;

correcting for orientation of the sensors;

determining cadence of the human subject's gait, including (i) calculating a motion signal based on the accelerometer data and the gyroscope data (ii) detecting stationary time periods wherein the motion signal falls below a threshold value (iii) selecting a midpoint in each stationary time period and (iv) calculating cadence of each step between midpoints in each stationary time period;

determining gait parameters for the human subject based on computing stride length and step height for each step in the human subject's gait based on the sensor data, including performing integration operations on the accelerometer data to acquire position data and calculating the human subject's stride length and step height based on the position data;

calculating one or more of variability and asymmetry in the human subject's gait based on the stride length and the cadence for each step between midpoints in each stationary time period; and storing the gait parameters and variability and asymmetry thereof in the system memory.

26. The method of claim 24, wherein said mobile communication device is adapted to be hand held by the human subject or attached to said human subject during performance of one or more of an evaluation exercise and a training exercise.

27. The method of claim 25, further comprising providing by said mobile device at least one of an auditory stimulus, a visual stimulus and a tactile stimulus to said human subject for providing feedback in real time to the human subject during performance of one or more of said evaluation exercises and said training exercises, the feedback including one or more of the gait parameters.

28. The method of claim 24, further comprising receiving software updates by said mobile communication device for at least one of said balance evaluation subsystem, said expert subsystem and said training subsystem, said software updates being sent by said remote subsystem.

29. The method of claim 28, wherein said software updates are sent daily and wherein said software updates include updates to said exercise plan.

30. The method of claim 24, further comprising coupling a remote interface to one or more of said mobile communication device and said remote server via a wide area network, said remote interface being configured to permit one or more of monitoring the performance of said human subject and controlling the evaluation and training of said human subject.

31. The method of claim 30, further comprising sending from one or more of said mobile communication device and said remote server to said remote interface a message identifying a risk of falling of said human subject.

32. The method of claim 31, wherein said risk of falling is determined by one or more of said balance evaluation subsystem, said training subsystem and said remote subsystem from said balance capabilities of said human subject.

33. The method of claim 24, further comprising providing motivational messages to said human subject on said display unit of said mobile communication device wherein said mobile communication device further comprises an incentive subsystem for generating said motivational messages.

34. The method of claim 24, further comprising, before evaluating balance capabilities, collecting information from said human subject regarding self-reported age, physical activity level and level of confidence regarding ability to maintain balance during physical activity, assessing using said information by said balance evaluation subsystem a risk of falling of said human subject during balance evaluation exercises, and wherein when said risk is above a threshold, providing a warning by said mobile communication device to said human subject to have a human companion available to provide for the safety of said human subject.

35. The method of claim 24, further comprising communicating from said mobile communication device to said human subject a message identifying that said human subject is at risk of falling.

36. The method of claim 35, wherein said risk of falling is determined by one or more of said balance evaluation subsystem, said training subsystem and said remote subsystem from said balance capabilities of said human subject.

37. The method of claim 24, further comprising calculating gait parameters of said human subject from data collected from said sensors during performance of said one or more balance evaluation exercises and balance training exercises by said human subject, said calculating being performed by one or more of said evaluation subsystem, said training subsystem and a remote subsystem on a remote server coupled to said mobile communication device by a wide area network.

38. The method of claim 37, further comprising providing feedback to said human subject regarding the gait of said human subject during performance of said one or more balance evaluation exercises and balance training exercises, wherein said feedback is provided during said performance of said one or more balance evaluation exercises and balance training exercises.

39. The method of claim 37, wherein said gait parameters include any selection of stride length, stride width, foot height, step cadence, walking speed, and measures of variabilities or asymmetries of stride length, stride width, foot height, step cadence and walking speed, wherein said variabilities or asymmetries include a measure of one or more of stride-to-stride variabilities or asymmetries and left-leg-to-right-leg variabilities or asymmetries.

40. A method of evaluating and training human balance, comprising:
at a mobile communication device comprising a computer processor, a system memory, a display unit, a network interface comprising one or more communication modules adapted to communicate over a wide area network, and a combination of sensors for measuring movement and rotation of the mobile communication device, the combination of sensors including (i) a 3-axis gyroscope adapted for measuring orientation and angular velocity and (ii) a 3-axis accelerometer adapted for measuring acceleration, the combination of sensors configured to measure sensor data characterizing movement of a human subject, the sensor data comprising one or more of gyroscope data and accelerometer data:
receiving data collected when said human subject is performing one or more balance evaluation exercises at a balance evaluation subsystem on the mobile communication device adapted for evaluating balance capabilities of the human subject, the data including data received from one or more of the combination of sensors and the human subject's interactions with the mobile communication device, the balance evaluation subsystem configured to evaluate the collected data and to provide a balance evaluation for the human subject based thereon,
prescribing an exercise plan for the human subject at an expert subsystem based on the balance evaluation provided by the balance evaluation subsystem, the exercise plan comprising one or more balance training exercises tailored for improving balance of the human subject;
administering to the human subject the prescribed exercise plan received from the expert subsystem, using a training subsystem, the prescribed exercise plan administered as an interactive exercise plan including one or more balance training exercises for said human subject; and
providing one or more cognitive challenges for dual tasking to actively engage the human subject's mind during performance of one or more balance evaluation exercises and balance training exercises, including (i) communicating a cognitive challenge to the human subject during performance of one or more balance evaluation exercises and balance training exercises and receiving performance data while the human subject is under the cognitive challenge, (ii) determining differences in the performance data for the human subject under the cognitive challenge with performance data under conditions without the cognitive challenge, and (iii) evaluating the determined differences in the performance data to ascertain an amount of variability in the human subject's performance during times when the human subject's attention is focused away from performing the balance evaluation or training exercises by the cognitive challenge,
wherein the human balance testing and training system enables the human subject using the mobile communication device to evaluate balance and to receive one or more exercise plans tailored for improving balance of the human subject to reduce risk of falls.

41. The method of claim 40, further comprising:
loading and validating the sensor data comprising the gyroscope data and the accelerometer data;
correcting for orientation of the sensors;
determining cadence of the human subject's gait, including (i) calculating a motion signal based on the accelerometer data and the gyroscope data (ii) detecting stationary time periods wherein the motion signal falls below a threshold value (iii) selecting a midpoint in each stationary time period and (iv) calculating cadence of each step between midpoints in each stationary time period;
determining gait parameters for the human subject based on computing stride length and step height for each step in the human subject's gait based on the sensor data, including performing integration operations on the accelerometer data to acquire position data and calculating the human subject's stride length and step height based on the position data;
calculating one or more of variability and asymmetry in the human subject's gait based on the stride length, step height and the cadence for each step between midpoints in each stationary time period; and
storing the gait parameters and variability and asymmetry thereof in the system memory.

42. The method of claim 41, wherein said gait parameters include any selection of stride length, stride width, foot height, step cadence, walking speed, and measures of variabilities or asymmetries of stride length, stride width, foot height, step cadence and walking speed, wherein said variabilities or asymmetries include a measure of one or more of stride-to-stride variabilities or asymmetries and left-leg-to-right-leg variabilities or asymmetries.

43. The method of claim 41, wherein said determining one of said initial training program or said modified training program uses as data input at least said gait parameters of said human subject.

44. The method of claim 41, further comprising providing feedback to said human subject regarding the gait of said human subject during performance of said one or more balance evaluation exercises and balance training exercises, wherein said feedback is provided during said performance of said one or more balance evaluation exercises and balance training exercises.

45. The method of claim 40, wherein one or more sensors of said combination of sensors are configured to be attached to said human subject at one or more of ankles and upper body.

46. The method of claim 40, further comprising providing by said mobile device at least one of an auditory stimulus, a visual stimulus and a tactile stimulus to said human subject for providing feedback in real time to the human subject during performance of one or more of said balance evaluation exercises and said balance training exercises, the feedback including one or more of the gait parameters.

47. The method of claim 41, further comprising receiving software updates by said mobile communication device for at least one of said evaluation subsystem, said expert subsystem and said training subsystem, said software updates being sent by said remote subsystem.

48. The method of claim 47, wherein said software updates are sent daily and wherein said software updates include updates to said exercise plan.

49. The system of claim 47, wherein said remote subsystem is further configured to calculate gait parameters of said human subject from data collected from said sensors.

50. The method of claim 41, further comprising coupling a remote interface to one or more of said mobile communication device and said remote server via a wide area network, said remote interface being configured to permit one or more of monitoring the performance of said human subject and controlling the evaluation and training of said human subject.

51. The method of claim 50, further comprising sending from one or more of said mobile communication device and said remote server to said remote interface a message identifying a risk of falling of said human subject.

52. The method of claim 51, wherein said risk of falling is determined by one or more of said evaluation subsystem, said training subsystem and said remote subsystem from said balance capabilities of said human subject.

53. The method of claim 41, further comprising providing motivational messages to said human subject on said display unit of said mobile communication device wherein said mobile communication device further comprises an incentive subsystem for generating said motivational messages.

54. The method of claim 41, further comprising measuring movement of said human subject by device sensors during performance of one or more of an evaluation exercise and a training exercise, wherein said mobile communication device comprises the device sensors.

55. The method of claim 54, wherein said mobile communication device is adapted to be hand held by said human subject during performance of one or more of an evaluation exercise and a training exercise.

56. The method of claim 54, wherein said mobile communication device is adapted to be attached to said human subject during performance of one or more of an evaluation exercise and a training exercise.

57. The system of claim 54, wherein said sensors include one or more of said device sensors.

58. The method of claim 41, further comprising, before evaluating balance capabilities, collecting information from said human subject regarding self-reported age, physical activity level and level of confidence regarding ability to maintain balance during physical activity, assessing using said information by said evaluation subsystem a risk of falling of said human subject during balance evaluation exercises, and wherein when said risk is above a threshold, providing a warning by said mobile communication device to said human subject to have a human companion available to provide for the safety of said human subject.

59. The method of claim 41, further comprising communicating from said mobile communication device to said human subject a message identifying that said human subject is at risk of falling.

60. The method of claim 59, wherein said risk of falling is determined by one or more of said evaluation subsystem, said training subsystem and said remote subsystem from said balance capabilities of said human subject.

61. The system of claim 1 wherein the balance evaluation comprises a balancing index configured to provide a numerical measure of the human subject's balance capabilities, the balancing index including one or more of a static balancing factor, a dynamic balancing factor, a strength factor and a cognitive balancing factor.

62. The system of claim 61 wherein the dynamic balancing factor is measured by the variance in the human subject's gait parameters while the human subject is performing one or more of the balance evaluation exercises and the balance training exercises.

63. The system of claim 11 wherein additional analysis is performed on the gait parameters to determine regularity, unpredictability, and self-similarity of time series data relating to the human subject's gait.

64. The system of claim 63 wherein the additional analysis comprises detrended fluctuation analysis (DFA) or entropy analysis (ApEn) performed on the gait parameters.

65. The system of claim 11 wherein the sensor data is processed by the mobile application or a remote computer server to determine the human subject's overall average speed of walking.

66. The system of claim 11 wherein gait speed of the human subject is measured at intervals to identify changes in gait speed as an indicator of increased risk of falling.

67. The system of claim 11 wherein the gait parameters are communicated over the wide area network to one or more external individuals, including the human subject's caregiver, family, trainer or doctor.

* * * * *